(12) United States Patent
Meier et al.

(10) Patent No.: US 10,336,547 B2
(45) Date of Patent: Jul. 2, 2019

(54) SAMPLE CONTAINER HANDLING DEVICE

(71) Applicant: Roche Diagnostics Operations, Inc., Indianapolis, IN (US)

(72) Inventors: Reto Andrin Meier, Stuttgart (DE); Alina Iwan, Tiefenbronn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 17 days.

(21) Appl. No.: 15/713,728

(22) Filed: Sep. 25, 2017

(65) Prior Publication Data
US 2018/0099812 A1 Apr. 12, 2018

(30) Foreign Application Priority Data
Oct. 7, 2016 (EP) .................................. 16192909

(51) Int. Cl.
| | | |
|---|---|---|
| *B07C 5/36* | (2006.01) | |
| *B65G 15/12* | (2006.01) | |
| *B65G 43/08* | (2006.01) | |
| *B65G 47/34* | (2006.01) | |
| *B65G 47/82* | (2006.01) | |
| *B65G 15/22* | (2006.01) | |
| *G01N 35/04* | (2006.01) | |
| *B07C 3/06* | (2006.01) | |

(52) U.S. Cl.
CPC ............... *B65G 15/22* (2013.01); *B07C 5/36* (2013.01); *B07C 5/362* (2013.01); *B65G 15/12* (2013.01); *B65G 43/08* (2013.01); *B65G 47/34* (2013.01); *B65G 47/82* (2013.01); *B07C 3/065* (2013.01); *B65G 2201/0235* (2013.01); *G01N 35/04* (2013.01); *G01N 2035/0401* (2013.01); *G01N 2035/0465* (2013.01); *G01N 2035/0484* (2013.01); *G01N 2035/0493* (2013.01)

(58) Field of Classification Search
CPC ........ B65G 15/22; B65G 15/12; B65G 43/08; B65G 47/34; B65G 47/47; B65G 47/82; B07C 5/36
USPC .................... 198/370.08, 598, 817
See application file for complete search history.

(56) References Cited

U.S. PATENT DOCUMENTS

| | | | | |
|---|---|---|---|---|
| 4,750,620 A | | 6/1988 | Braschos | |
| 5,018,619 A | * | 5/1991 | Wilson .................... | B07B 13/05 198/839 |
| 5,058,723 A | * | 10/1991 | Hosch .................. | B65G 47/846 198/370.08 |
| 5,388,705 A | * | 2/1995 | Fine ......................... | B07C 5/361 198/367 |
| 5,797,478 A | * | 8/1998 | Gambetti ................ | B65B 35/46 198/441 |
| 6,041,910 A | * | 3/2000 | Avery .................. | B65G 47/846 198/370.07 |
| 6,822,181 B2 | * | 11/2004 | Linton .................. | B07C 5/3408 209/523 |

(Continued)

FOREIGN PATENT DOCUMENTS

DE 10007627 A1 9/2001
EP 2813445 A1 12/2014

*Primary Examiner* — Douglas A Hess
(74) *Attorney, Agent, or Firm* — Roche Diagnostics Operations, Inc.

(57) ABSTRACT

A sample container handling device is presented. The device comprises a linear transport unit and a release unit comprising a release blade segment. The release blade segment is rotated in a constant rotational direction.

13 Claims, 2 Drawing Sheets

(56) References Cited

U.S. PATENT DOCUMENTS

| | | | |
|---|---|---|---|
| 7,467,705 B2 * | 12/2008 | Lutz | B65G 17/24 |
| | | | 198/408 |
| 7,992,700 B2 * | 8/2011 | Thoonsen | B65G 47/82 |
| | | | 198/370.08 |
| 9,248,980 B2 * | 2/2016 | Pedrazzini | B65G 47/46 |
| 9,445,505 B2 * | 9/2016 | Liu | H05K 3/0082 |
| 9,902,567 B1 * | 2/2018 | Zimmer et al. | B65G 47/82 |
| | | | 198/370.07 |
| 2004/0109747 A1 | 6/2004 | Charpentier | |
| 2006/0144764 A1 | 7/2006 | Large et al. | |

* cited by examiner

SAMPLE CONTAINER HANDLING DEVICE

CROSS-REFERENCE TO RELATED APPLICATIONS

This application is a continuation of EP 16192909.6, filed Oct. 7, 2016, which is hereby incorporated by reference.

BACKGROUND

The present disclosure relates to a sample container handling device comprising a linear transport unit and a release unit.

Known sample container handling devices are adapted to push a sample container being transported by the linear transport unit away from the transport unit using a release blade segment. After the pushing operation, the release blade segment is typically rotated back to an initial position.

There is a need for a sample container handling device providing for a reliable and fast operation.

SUMMARY

According to the present disclosure, a sample container handling device is presented. The sample container device can comprise a linear transport unit adapted to transport sample containers in horizontal orientation to a release position and a release unit comprising a release blade segment adapted to abut a respective sample container in the release position along a side line and to push the sample container away from the transport unit. The release unit can be configured to rotate the release blade segment around an axis such that a plurality of sample containers are sequentially pushed away from the linear transport unit while the release blade segment is rotating in a constant rotational direction. The linear transport unit can be configured to sequentially transport sample containers to the release position synchronized with the rotation of the release blade segment.

Accordingly, it is a feature of the embodiments of the present disclosure to provide for a sample container handling device providing for a reliable and fast operation. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
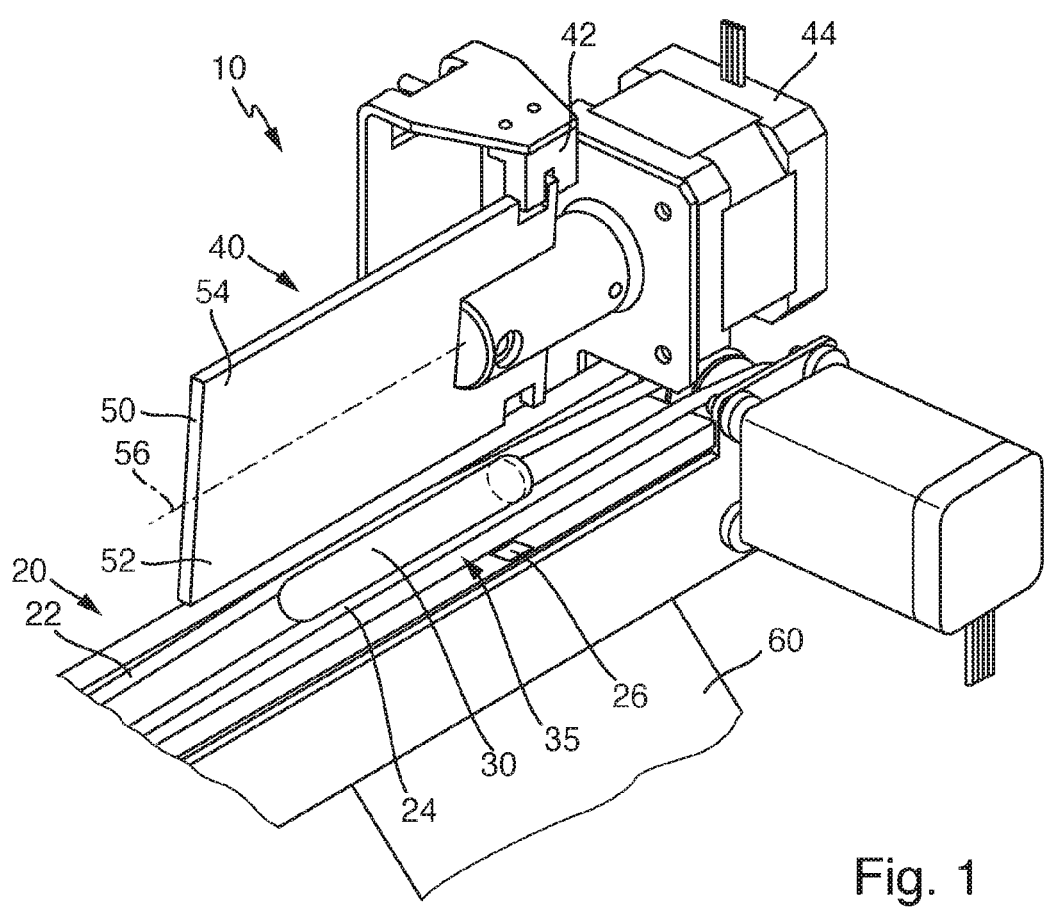
FIG. 1 illustrates a sample container handling device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A sample container handling device is presented. The sample container handling device can comprise a linear transport unit adapted to transport sample containers in horizontal direction to a release position.

The linear transport unit can comprise a release unit comprising at least one release blade segment adapted to abut a respective sample container in the release position along a side line and to actively push the sample container away from the transport unit. The release blade segment can be adapted to push the sample container substantially perpendicular to the orientation of the sample container and/or substantially perpendicular to a transport direction of the sample container on the linear transport unit.

The release unit can be configured to rotate the release blade segment around an axis such that a plurality of sample containers can be sequentially pushed away from the linear transport unit while the release blade segment is rotating in a constant rotational direction.

The linear transport unit can be configured to sequentially transport sample containers to the release position synchronized with the rotation of the release blade segment, in particular such that the sample containers consecutively approaching the release position can be pushed away from the transport unit by release blade segments consecutively passing the release position.

The release position may be a position at which the release blade segment abuts a respective sample container along the complete side line of the respective sample container, in particular such that a rotation of the respective sample container can be avoided when the sample container is pushed away from the transport unit by the release blade segment.

The release unit may be configured to rotate the release blade segment only when a respective sample container is/has reached the release position.

A constant rotational direction can be upheld by the sample container handling device. In prior art embodiments, there exists a risk that a following sample container transported by the linear transport unit is unintentionally hit by the release blade segment rotating back to its initial position. Due to the constant rotational direction, this risk can be avoided. Consequently, the present disclosure can significantly improve reliability of operation.

According to an embodiment, the linear transport unit can comprise two parallel belts adapted to move synchronously to transport the sample containers. The belts may move in a constant linear direction in order to transport the sample containers. A belt based linear transport unit is e.g. disclosed in EP 2 813 445 A1 and is incorporated herein by reference.

According to an embodiment, the axis can be a horizontal axis. The axis can be substantially parallel to the transport direction. The two belts may lie in a common belt plane, wherein the axis may lie in an axis plane substantially perpendicular to the belt plane and the axis plane located substantially in the middle between the two belts.

The release unit may comprise a further release blade segment. The release blade segment and the further release blade segment can be part of a flat release blade. This can allow for two push away operations during one 360° turn.

According to an embodiment, the axis can be positioned, or extends, between the release blade segment and the further release blade segment on the release blade.

According to an embodiment, the release unit can comprise a plurality of release blades, each comprising two release blade segments. This can further increase the number of push away operations during one 360° turn.

The axis may be positioned, or may extend, between each two release blade segments of each release blade. The release blades may be angularly oriented in equidistant angles. This can simplify operation.

According to an embodiment, each two release blade segments of a respective release blade can have equivalent shapes. This can also simplify operation.

According to an embodiment, the sample container handling device can comprise an oblique slide which can, for example, be embodied as an inclined plane with a sloping level. The oblique slide may be positioned adjacent to the release position such that a sample container pushed away from the linear transport unit can slide downwardly along the oblique slide. Using an oblique slide may help stabilizing movement of the pushed away sample containers and can direct them to a specific position for further handling.

According to an embodiment, the release blade segments, or the release blades, can be made of aluminum or plastic material. Such materials have been proven suitable for typical applications.

According to an embodiment, the release unit can comprise a first sensor, e.g. a fork light barrier, for sensing the rotational position of the release blade segment. This can, for example, support synchronizing the rotation of the release blade segment, or of the release blades, with the operation of the linear transport unit.

According to an embodiment, the linear transport unit can comprise a second sensor, e.g. a capacitive sensor, for detecting presence of a sample container in the release position. This can support controlling and synchronizing operation.

According to an embodiment, the release unit can be configured to rotate the release blade segment responsive to the second sensor detecting presence of a sample container in the release position. This can allow for a reliable and efficient operation.

Conventional release blade segments are operated in a manner similar to a pendulum, meaning that the release blade segments rotate from a starting position to a release position, rotate back to the starting position and so forth. It has been found that such an operation can cause problems in that a following sample container is unintentionally hit when the release blade segment rotates back to its starting position. This problem can be avoided by rotating the release blade segment only in one direction, i.e. avoiding a change in the rotational direction.

Referring initially to FIG. 1, FIG. 1 shows a sample container handling device 10 according to a first embodiment. The sample container handling device 10 can comprise a linear transport unit 20. The linear transport unit 20 can comprise a first belt 22 and a second belt 24. The belts 22, 24 can extend in substantially parallel to each other and can be adapted to move synchronously to the right side of FIG. 1 in order to transport sample containers 30. The sample containers 30 can be lying in a horizontal orientation on the belts 22, 24. One sample container 30 is shown exemplarily in FIG. 1. It is positioned in a release position 35 from which it may be released in a manner discussed further below.

The linear transport unit 20 can further comprise a first sensor in the form of a capacitive sensor 26 positioned below the release position 35. The capacitive sensor 26 can be adapted to detect presence of a sample container 30 in the release position 35 so that a release operation can be initiated. By the release operation the sample container 30 can be pushed from the linear transport unit 20.

For releasing the sample container 30, the sample container handling device 10 can comprise a release unit 40. The release unit 40 can comprise a release blade 50. The release blade 50 can comprise a first release blade segment 52 and a second release blade segment 54, which together can form the release blade 50. The release blade segments 52, 54 can be separated by an axis 56. The axis 56 can be oriented in a substantially horizontal direction and can form a rotational axis of the release blade 50.

The release unit 40 can further comprise an electric motor 44 adapted to rotate the release blade 50 around its axis 56. The electric motor 54 can be adapted to rotate the release blade 50 in a constant rotational direction.

The release unit 40 can further comprise a second sensor in form of a release blade sensor 42 embodied, for example, as a fork light barrier. The release blade sensor 42 can be adapted to detect presence of a release blade segment 52, 54 in order to control rotation of the release blade 50.

Adjacent to the release position 35, an oblique slide 60 can be arranged. When the electric motor 54 rotates the release blade 50, the sample container 30 can be pushed away from the linear transport unit 20 towards the oblique slide 60 and then can slide down the oblique slide 60 to a position where the sample container 30 can be further processed.

The linear transport unit 20 can sequentially transport sample containers 30 to the release position 35. The release blade 50 can be rotated by the motor 44 synchronized with the operation of the linear transport unit 20. In order to synchronize the operation, the sensors 26, 42 can be used.

Every time a sample container 30 is positioned at the release position 35, one of the two release blade segments 52, 54 can abut the sample container 30 along its side line. With further rotation of the release blade 50, the respective sample container 30 can be pushed away from the belts 22, 24 in a substantially perpendicular direction with reference to the transportation direction of the linear transport unit 20. The sample container 30 can then fall on the oblique slide 60 and slide away to the next handling place.

Figure 2:
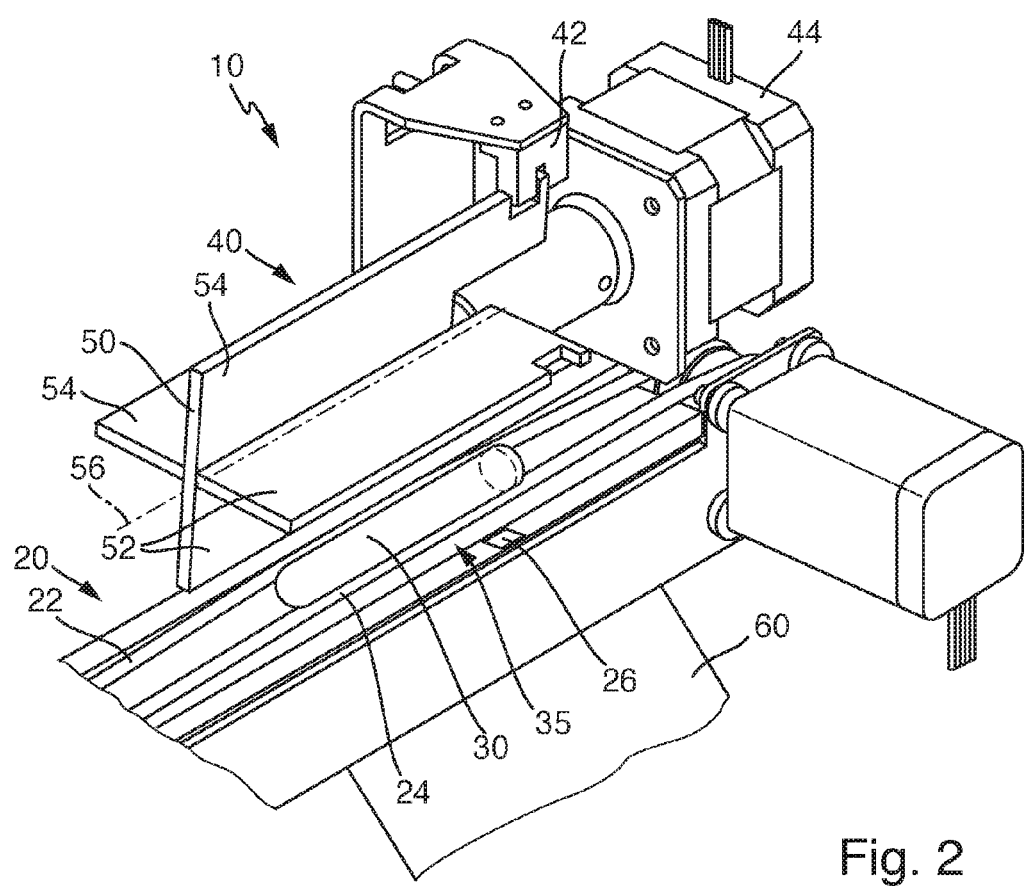
FIG. 2 illustrates a sample container handling device according to another embodiment of the present disclosure.

FIG. 2 shows a sample container handling device 10 according to a further embodiment. Elements having the same function as elements already depicted in FIG. 1 are denoted with equal reference signs.

The release unit 40 of the embodiment shown in FIG. 2 can comprise a second release blade 50 having two release blade segments 52, 54 having equivalent shapes. Both release blades 50 can be angularily oriented with equidistant angles here about 90 degrees.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A sample container handling device, the sample container device comprising:
   a linear transport unit adapted to transport sample containers in horizontal orientation to a release position; and
   a release unit comprising a release blade segment adapted to abut a respective sample container in the release position along a side line and to push the sample container away from the transport unit, wherein the release unit is configured to rotate the release blade segment around an axis such that a plurality of sample containers are sequentially pushed away from the linear transport unit while the release blade segment is rotating in a constant rotational direction and wherein the linear transport unit is configured to sequentially transport sample containers to the release position synchronized with the rotation of the release blade segment, wherein the release unit comprises a first sensor for sensing a rotational position of the release blade segment.

2. The sample container handling device according to claim 1, wherein the linear transport unit comprises two parallel belts adapted to move synchronously to transport the sample containers.

3. The sample container handling device according to claim 1, wherein the axis is a horizontal axis.

4. The sample container handling device according to claim 1, wherein the release unit comprises a further release blade segment, wherein the release blade segment and the further release blade segment are part of a flat release blade.

5. The sample container handling device according to claim 4, wherein the axis is positioned between the release blade segment and the further release blade segment on the release blade.

6. The sample container handling device according to claim 4, wherein each two release blade segments of a respective release blade have equivalent shapes.

7. The sample container handling device according to claim 4, wherein the release blade segments or the release blades are made of aluminum or plastic material.

8. The sample container handling device according to claim 1, wherein the release unit comprises a plurality of release blades, each comprising two release blade segments.

9. The sample container handling device according to claim 8, wherein the axis is positioned between each two release blade segments of each release blade.

10. The sample container handling device according to claim 8, wherein the release blades are angularily oriented with equidistant angles.

11. The sample container handling device according to claim 1, further comprises
    an oblique slide positioned adjacent to the release position such that a sample container pushed away from the linear transport unit slides downwardly along the oblique slide.

12. The sample container handling device according to claim 1, wherein the linear transport unit comprises a second sensor for detecting presence of a sample container in the release position.

13. The sample container handling device according to claim 12, wherein the release unit is configured to rotate the release blade segment responsive to the second sensor detecting presence of a sample container in the release position.

* * * * *